United States Patent [19]

Brown

[11] Patent Number: 5,741,527

[45] Date of Patent: Apr. 21, 1998

[54] VETERINARY TOPICAL COMPOSITIONS AND METHODS OF USE

[76] Inventor: Paul K. Brown, 1101 River Bend Rd., Haughton, La. 71037

[21] Appl. No.: 800,563

[22] Filed: Feb. 18, 1997

[51] Int. Cl.$^6$ ............................ A61K 33/28; A61K 35/78
[52] U.S. Cl. ................ 424/645; 424/195.1; 514/887; 514/936; 514/947
[58] Field of Search ........................ 424/645, 195.1; 514/887, 936, 947

[56] References Cited

U.S. PATENT DOCUMENTS

| | | | |
|---|---|---|---|
| 4,353,896 | 10/1982 | Levy | 424/195.1 |
| 4,567,044 | 1/1986 | DeSantis | 424/94.65 |
| 4,927,641 | 5/1990 | Knight | 424/665 |
| 5,028,429 | 7/1991 | Gochenouer | 424/195.1 |

OTHER PUBLICATIONS

Schuh, Joann C. L. et al., "Concurrent Mercuric Blister and Dimethyl Sulphoxide (DMSO) Application as a Cause of Mercuric Toxicity in Two Horses," Equine Vet. Journal, vol. 20(1), pp. 68–71, 1988.

The Merck Veterinary Manual, 7th Ed., Merck & Co., Inc., Rahway (NJ), pp. 1374 and 1530, 1991.

AISUP, Eric M., "DMSO," J. Am. Vet. Med. Assoc., vol. 185(9), pp. 1011–1014, 1984.

*Primary Examiner*—John Pak

[57] ABSTRACT

The present invention relates to novel veterinary topical compositions, methods of making the compositions, and methods of using the compositions in the treatment of bone, muscle and connective tissue injuries, as well as respiratory ailments, in animals, particularly horses, dogs, and goats. The compositions comprise isopropyl alcohol, mercuric chloride and dimethylsulfoxide (DMSO), and may further comprise herbs. Light training can typically be resumed beginning about 24 hours after applying the composition to the injured area of the animal.

3 Claims, No Drawings

VETERINARY TOPICAL COMPOSITIONS AND METHODS OF USE

FIELD OF THE INVENTION

The present invention provides novel veterinary topical compositions for use in the treatment of animal injuries. The invention further provides methods of making the compositions, and methods of treating various bone, muscle, tendon, and other injuries/ailments by topical application of the compositions. The invention is particularly useful in treating injuries in horses, dogs, and goats. The compositions broadly comprise isopropyl alcohol, mercuric chloride and DMSO, and may further comprise herbs such as basil, bay, mint, or combinations thereof.

BACKGROUND OF THE INVENTION

Liniments are well known for their use in the alleviation of pain and soreness resulting from various injuries in animals. Such liniments are generally topically applied either prophylactically or after injury has occurred. Liniments can be used in various forms, such as lotions, creams, jellies, liquids, gels or aerosols.

Dimethylsulfoxide (DMSO) is a highly polar, stable, hygroscopic organic liquid with exceptional solvent properties. DMSO has been extensively investigated for possible industrial and/or biological utility. DMSO can easily penetrate the dermal barrier of animals. As such, it has been tested in topical preparations as a carrier for medicinal/therapeutic agents. In addition to its ability to act as an effective carrier, DMSO alone has also been demonstrated to provide therapeutic benefits in certain settings. Some DMSO-containing liniments have been disclosed in the prior art for the treatment of horse injuries. (See, for example, U.S. Pat. No. 4,567,044 and U.S. Pat. No. 4,927,641)

Mercuric chloride has been used in certain chemical formulations, such as leg "paints" or leg "blisters", as a means of treating certain horse injuries. (See, for example, U.S. Pat. No. 5,028,429) It is applied to the skin for the purpose of creating intense local inflammation in an already chronically inflamed area. The blistering process causes an increase in the blood supply to the blistered area, which becomes swollen and hot. After the effects of the blister subside, the original area of inflammation or swelling often subsides as well.

SUMMARY OF THE INVENTION

The present invention broadly concerns topical compositions, typically referred to as liniments, for treating injuries in animals, notably horses, dogs, and goats. The invention also concerns methods of making and using such compositions.

One broad aspect the invention resides in liniments or other topical compositions which comprise isopropyl alcohol, dimethyl sulfoxide (DMSO) and mercuric chloride. Other pharmaceutically compatible and acceptable components may also be present and advantageous. Vehicles such as water, natural and synthetic polymers, oils, waxes, alcohols, glycols, gelling agents, etc. may be desirable for ease in handling, assurance of adherence to the animal, etc.

In general, compositions of the invention should contain sufficient quantities of its principal components to have a therapeutic effect on an injury or other affliction causing a problem for an animal. It is not fully understood how the components interact to produce healing, pain reduction, etc., but the most active components appear to be the mercuric chloride and the DMSO. It has been found that from about 5 to 30 wt. % mercuric chloride and about 0.1 to 5.0 wt. % DMSO embrace the more effective concentrations for these components. Furthermore, from about 10 to 20 wt. % of the mercuric chloride and from about 0.5 to 2.0 wt. % of the DMSO are the most attractive concentrations of these materials. The preferred third component is isopropyl alcohol because of its ability, under proper conditions, to solubilize the mercuric chloride and DMSO.

In another aspect of the invention, there is provided a method of making the composition. Mercuric chloride and DMSO are mixed or blended with isopropyl alcohol or other suitable vehicles to form a homogeneous mixture. Preferably, isopropyl alcohol is warmed sufficiently to dissolve or otherwise disperse mercuric chloride, and DMSO is then added to the resulting dispersion. Preferably, the alcohol is heated to a temperature from about 35° C. to 50° C. prior to addition of mercuric chloride and DMSO.

In yet another aspect of the invention, the compositions of the invention are applied in one or more steps, separated by intervals of at least several hours, to enable each application to exert a therapeutic effect. In general, swelling of the treated area will be observed several hours after applying the compositions, followed by drainage of the area thereafter. If swelling occurs without drainage, additional applications of the composition may be necessary or desired. Intervals of about twelve hours between applications have proven to be very beneficial and effective. Moreover, two applications have frequently been found to be sufficient for many injuries, however the number of applications may be as many as five or more. Moderate exercise of the animal during such intervals is also important. Exercise generally begins about 24 hours after the first application of the composition and is continued thereafter at least once daily or until swelling of the injured area has been reduced and the animal's mobility improved.

In yet a further aspect of the present invention, there is provided a method of treating animal respiratory ailments comprising topically applying to the throat area a composition comprising isopropyl alcohol, mercuric chloride, and DMSO. Typically, the composition is applied once daily for three consecutive days.

DESCRIPTION OF ILLUSTRATIVE EMBODIMENTS

In one embodiment of the present invention, veterinary liniment compositions are provided for use in the effective treatment of bone, muscle, tendon, ligament, cartilage, joint, and other related injuries in animals. The compositions comprise isopropyl alcohol, mercuric chloride and DMSO, and may also include one or more herbs. Optionally, food coloring or dye may be added. In a preferred embodiment, the compositions comprise from about 65% to about 95% isopropyl alcohol, from about 5% to about 30% mercuric chloride, and from about 0.1% to about 5% DMSO. More preferably, the compositions comprise from about 80% to about 88% isopropyl alcohol, from about 12% to about 18% mercuric chloride, and from about 0.5% to about 2% DMSO. In a most preferred embodiment, the compositions comprise about 83.4% by weight isopropyl alcohol, about 15.9% mercuric chloride, and about 0.7% DMSO.

The compositions of the present invention may optionally contain one or more herbs. Typically, the herbs comprise from about 0.001% to 0.25% basil, from about 0.001% to 0.25% bay, from about 0.001% to 0.25% mint, or combinations thereof. In a more preferred embodiment, the herbs comprise about 0.1% basil, 0.1% bay, 0.1% mint, or combinations thereof.

Other pharmaceutically acceptable or compatible components may be present and advantageous in the compositions without departing from the scope of the disclosed invention. Solvents other than isopropyl alcohol which are capable of solubilizing mercuric chloride and DMSO may, for example, represent suitable alternatives. Vehicles such as natural and synthetic polymers, oils, waxes, glycols, gelling agents, etc. may be desirable for ease in handling, assurance of adherence to the animal, etc. Additionally, antiseptics may be advantageously included in the compositions, or administered after treatment with the compositions, to minimize the risk of infection to the animal.

In a further embodiment of the present invention, there is provided a method of preparing the liniment compositions. The compositions are prepared by mixing or blending isopropyl alcohol and mercuric chloride, and subsequently adding DMSO. Prior to the addition of mercuric chloride to isopropyl alcohol, the isopropyl alcohol is generally heated to a temperature sufficient to effectively dissolve the mercuric chloride. Preferably, the isopropyl alcohol is heated to about 35° to 50° C. prior to the addition of mercuric chloride. About 10 to 90 minutes of mixing may be necessary to completely dissolve the mercuric chloride in the isopropyl alcohol. In a preferred embodiment, the isopropyl alcohol and mercuric chloride are mixed for about 45 minutes at a temperature of about 43° C. DMSO is preferably added to the isopropyl alcohol after the mercuric chloride has already been added and substantially dispersed.

In yet a further embodiment of the present invention, there are provided methods of using the compositions for treating injured animals. The compositions have been found to be useful in treating a variety of animal injuries, for example those affecting bones, muscles, tendons, ligaments, cartilage, joints, as well as other areas of injury manifested by swelling and the accumulation of fluid. The compositions are particularly useful in the treatment of such injuries in horses, dogs, and goats. However, it is expected that the compositions will be applicable to the treatment of similar injuries in other animal species. For brevity and clarity, the discussion which follows relates the use of the present compositions for treating horse injuries. More particularly, the horse injuries which have been found to be effectively treatable with the present compositions include, but are not limited to lameness, shin bucks, splints, osselets, bone chips, bony enlargements, sprained ligaments, sprained tendons, gravels, abscesses, injured elbows, and injured stifles.

The affected area is generally clipped, cleaned and thoroughly dried. The horse should remain calm during application of the liniment compositions, and for several hours after application. The compositions may prove to be less effective if the horse digs excessively, walks the stall, or is generally agitated. In some instances sedation may be desirable.

The specific area on the animal to which the compositions are applied varies depending upon the injury. For many injuries, it is sufficient to apply the compositions directly on and closely adjacent to the injured area. This is typically true, for example, in treating stifles, injured elbows, gravels, and abscesses. However, for many leg and knee injuries, it is preferred that the compositions be applied to the entire leg rather than only to the obviously injured area. In addition, if an injury is apparent only on one front leg, it is preferred that both front legs be treated. Similarly, if the injury is only apparent on one back leg, preferably both back legs are treated. This is helpful in keeping the horse balanced, so as not to favor the leg opposite the injured one.

The compositions are typically applied one or more times, separated by intervals of at least several hours. The total number of applications needed will depend upon the particular injury/ailment being treated and upon the nature of the animal's response to the composition. Frequently, soreness/injury to the elbows or stifles can be effectively treated with a single application of the composition. Most injuries, however, will require two or more applications of the compositions.

Typically, within several hours of applying the compositions, the injured area will show considerable swelling in excess of any swelling which was already present. An effective method of monitoring the therapeutic response to the compositions relates to drainage of the swollen area. If, after several hours of applying the first treatment, drainage has occurred thereby causing some swelling to subside, no additional applications of the compositions may be needed. If, however, excessive swelling of the injured area persists without drainage, the compositions should be applied a second time to the same area about 6–18 hours after the first application. Thereafter, the animal should be checked daily for drainage of the swollen areas to determine whether additional applications are needed. Subsequent applications are typically given once daily, following exercise, until drainage is observed.

In some situations, it may be preferred to apply the composition initially to a large area within which the injury is contained, and then restricting any subsequent applications needed specifically to the injured region. When treating shin bucks or bowed tendons in horses, for example, the composition can be first applied from the coronet band to about an inch above the chestnut when treating the front legs, or from the coronet to just below the gaskin when treating the back legs. If after a second application of the composition, drainage has yet to occur, subsequent treatments are preferably applied to a smaller and more targeted area than for the first two applications. Thus, subsequent applications are restricted to the shins when treating shin bucks and to the tendons when treating bowed tendons, rather than applying the compositions to the entire legs.

Exercise is important in realizing the therapeutic benefits of the compositions. For some injuries, such as those to the elbows or stifles, exercise preferably begins immediately, or less than about one hour, after applying the compositions. For most other injuries, however, it is preferred that exercise be started about 24 hours after the first application of the composition. Light to moderate exercise at least once daily is recommended, preferably for about an hour at a time. Extended trotting can be very therapeutic. Turn-out or hot walking is excellent supportive therapy to light exercise. Daily exercise should be maintained for at least about 5 days and up to 25 or more days, until swelling has been reduced and the animal's mobility improved. When daily applications of the composition are given, the animal is preferably exercised subsequent to each such application.

In yet a further embodiment of the present invention, there is provided a method of treating respiratory ailments. It has been found that the present compositions can ameliorate the symptoms in a number of conditions in which breathing is impaired. For example, cribbing, roaring, heaves, coughing and other respiratory problems in horses may be effectively treated by applying the composition under the animal's throat approximately from ear to ear. It is preferable to apply the composition once daily for three consecutive days.

Generally, swelling and drainage is not observed when treating these conditions, and exercise is not required.

It is preferred that the horse be removed from all medications about 24–36 hours prior to applying the composition to the horse unless there are emergency circumstances. Anti-inflammatory drugs tend to interfere with the effectiveness of treatment. To ease skin dryness and irritation, an aloe-vera-containing shaving creme may be used as desired as a salve. Other topical applications may harm the efficacy of the compositions and may cause undesirable side effects. Other topicals preferably should not be used in conjunction with the compositions, with the exception of mild soap and water.

The following examples are included to illustrate certain preferred embodiments of the invention. It should be appreciated by those of skill in the art that the techniques disclosed in the examples which follow represent approaches which have been found to function effectively in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

A method of making an illustrative embodiment of the liniment composition is provided by the following specific example. This example involved the following steps:
1. Heating 743 g isopropyl alcohol to 43° C.;
2. Slowly adding 142 g mercuric chloride powder with continued stirring until completely dissolved;
3. Adding 6.6 g DMSO;
4. Adding about 1 g each of herb basil, bay and mint with continued stirring for approximately 5 minutes;
5. Adding 0.5 ml blue food coloring; and,
6. Cooling the resulting mixture.

EXAMPLE 2

TREATMENT OF LEGS AND KNEES: Clip legs from coronet band to an inch above the chestnut for treating the front legs or from the coronet to just below the gaskin when treating the back legs. Wash the legs thoroughly, making sure residues of other medications/products are removed. After the legs are thoroughly dry, apply the composition a first time to the clipped areas. About 12 hours later, check the injury for swelling and/or drainage. If drainage has occurred, no additional applications of the composition should be necessary. If swelling persists without drainage, however, apply the composition a second time. About 24 hours after the first application, moderate exercise should begin. Exercise at least once daily is recommended, with extended trotting being most therapeutic. If after two applications of the composition, swelling persists without drainage, subsequent applications of the compositions should be given once daily following exercise until drainage of the area is observed. Daily exercise should be maintained for at least about 5–25 days or until essentially all swelling has been reduced and the animal's mobility improved.

EXAMPLE 3

TREATMENT OF SHIN BUCKS: Clip legs from coronet band to an inch above the chestnut for treating the front legs or from the coronet to just below the gaskin when treating the back legs. Wash the legs thoroughly, making sure residues of other medications/products are removed. After the legs are thoroughly dry, apply the composition a first time to the clipped areas. About 12 hours later, check the injury for swelling and/or drainage. If drainage has occurred, no additional applications of the composition should be necessary. If swelling persists without drainage, however, apply the composition a second time. About 24 hours after the first application, moderate exercise should begin. Exercise at least once daily is recommended, with extended trotting being most therapeutic. If after two applications of the composition, swelling persists without drainage, subsequent applications of the composition should be given once daily following exercise until drainage of the area is observed. However, these subsequent applications of the composition should be restricted only to the shin areas of each leg rather than the entire leg. Daily exercise should be maintained for at least about 5–25 days or until essentially all swelling has been reduced and the animal's mobility improved.

EXAMPLE 4

TREATMENT OF BOWED TENDONS: Clip legs from coronet band to an inch above the chestnut for treating the front legs or from the coronet to just below the gaskin when treating the back legs. Wash the legs thoroughly, making sure residues of other medications/products are removed. After the legs are thoroughly dry, apply the composition a first time to the clipped areas. About 12 hours later, check the injury for swelling and/or drainage. If drainage has occurred, no additional applications of the composition should be necessary. If swelling persists without drainage, however, apply the composition a second time. About 24 hours after the first application, moderate exercise should begin. Exercise at least once daily is recommended, with extended trotting being most therapeutic. If after two applications of the composition, swelling persists without drainage, subsequent applications of the compositions should be given once daily following exercise until drainage of the area is observed. However, these subsequent applications of the composition should be restricted only to the tendon areas of each leg rather than the entire leg. Daily exercise should be maintained for at least about 5–25 days or until essentially all swelling has been reduced and the animal's mobility improved.

The liniment may be reapplied to both tendons approximately 45 days after the first application of the liniment. Swelling and drainage at this point indicate that the tendons are not completely healed or tight enough to withstand stressful exercise (for example, race or work).

EXAMPLE 5

TREATMENT OF GRAVELS AND ABSCESSES: Clip the coronet in a 2 inch strip. Wash the legs thoroughly, making sure residues of other medications/products are removed. After the legs are thoroughly dry, apply the composition a first time to the clipped areas. About 12 hours later, check the injury for swelling and/or drainage. If drainage has occurred, no additional applications of the composition should be necessary. If swelling persists without drainage, however, apply the composition a second time. About 24 hours after the first application, moderate exercise should begin. Exercise at least once daily is recommended, with extended trotting being most therapeutic. If after two applications of the composition, swelling persists without drainage, subsequent applications of the compositions should be given once daily following exercise until drainage of the area is observed. Daily exercise should be maintained for at least about 5–25 days or until essentially all swelling has been reduced and the animal's mobility improved.

EXAMPLE 6

TREATMENT OF ELBOWS: Apply the composition in a 2 inch area inside and outside of the elbow. Exercise immediately after applying the composition. Exercise at least once daily is recommended, with extended trotting being most therapeutic. Daily exercise should be maintained for at least about 5–25 days or until essentially all swelling has been reduced and the animal's mobility improved.

EXAMPLE 7

TREATMENT OF STIFLES: Clip an eight inch area from the ball of the stifle inside and outside of leg. Apply a light coating of the composition to the clipped area. Do not rub the composition into this area. Exercise the horse immediately after applying the composition. Exercise at least once daily is recommended, with extended trotting being most therapeutic. Daily exercise should be maintained for at least about 5–25 days or until essentially all swelling has been reduced and the animal's mobility improved.

The examples disclosed herein are provided merely to illustrate the present invention and should not be interpreted in any way to limit the scope of the invention. Those skilled in the art will recognize that various modifications can be made to the invention described herein while not departing from the spirit and scope of the present invention. For brevity and clarity, the examples have been limited to the treatment of horse injuries. However, similar treatment approaches are equally applicable to injuries in other animal species, including goats and dogs.

What is claimed is:

1. A topical composition for treatment of injuries in animals comprising isopropyl alcohol, mercuric chloride and DMSO, wherein said isopropyl alcohol comprises from about 65–95 wt. % of said composition, said mercuric chloride comprises from about 5–30 wt. % of said composition, and said DMSO comprises from about 0.1–5.0% wt. % of said composition.

2. The composition of claim 1 wherein said isopropyl alcohol comprises about 83.4 wt. % of said composition, said mercuric chloride comprises about 15.9 wt. % of said composition, and said DMSO comprises about 0.7 wt. % of said composition.

3. The composition of claim 1, further comprising at least one herb.

* * * * *